United States Patent
De Sousa Dias et al.

(10) Patent No.: US 9,434,708 B2
(45) Date of Patent: Sep. 6, 2016

(54) PROCESS FOR CARRYING OUT A REACTION INVOLVING A LIQUID REACTION MIXTURE

(71) Applicant: Furanix Technologies B.V., Amsterdam (NL)

(72) Inventors: Ana Sofia Vagueiro De Sousa Dias, Amsterdam (NL); Jan Cornelis Van Der Waal, Amsterdam (NL); Etienne Mazoyer, Amsterdam (NL)

(73) Assignee: FURANIX TECHNOLOGIES B.V. (NL)

( * ) Notice: Subject to any disclaimer, the term of this patent is extended or adjusted under 35 U.S.C. 154(b) by 146 days.

(21) Appl. No.: 14/369,485

(22) PCT Filed: Dec. 27, 2012

(86) PCT No.: PCT/NL2012/050932
§ 371 (c)(1),
(2) Date: Jun. 27, 2014

(87) PCT Pub. No.: WO2013/100768
PCT Pub. Date: Jul. 4, 2013

(65) Prior Publication Data
US 2014/0364634 A1 Dec. 11, 2014

Related U.S. Application Data

(60) Provisional application No. 61/580,845, filed on Dec. 28, 2011.

(30) Foreign Application Priority Data

Dec. 28, 2011 (NL) ..................................... 2008047

(51) Int. Cl.
| | | |
|---|---|---|
| C07D 307/48 | (2006.01) |
| B01J 21/08 | (2006.01) |
| B01J 29/08 | (2006.01) |
| B01J 29/18 | (2006.01) |
| B01J 29/40 | (2006.01) |
| B01J 29/60 | (2006.01) |
| B01J 29/70 | (2006.01) |

(52) U.S. Cl.
CPC .............. *C07D 307/48* (2013.01); *B01J 21/08* (2013.01); *B01J 29/08* (2013.01); *B01J 29/18* (2013.01); *B01J 29/40* (2013.01); *B01J 29/60* (2013.01); *B01J 29/7003* (2013.01); *B01J 29/7007* (2013.01)

(58) Field of Classification Search
CPC .............................. C07D 307/48; B01J 21/08
See application file for complete search history.

(56) References Cited

U.S. PATENT DOCUMENTS

| | | | |
|---|---|---|---|
| 3,152,998 A | 10/1964 | Moss | |
| 4,146,741 A | 3/1979 | Prichard | |
| 4,752,596 A | 6/1988 | Bergna et al. | |
| 4,861,743 A * | 8/1989 | Flank ...................... | B01J 29/84 423/305 |

FOREIGN PATENT DOCUMENTS

| | | |
|---|---|---|
| WO | 99/42214 A1 | 8/1999 |
| WO | 2007/104514 A2 | 9/2007 |
| WO | 2007/104515 A1 | 9/2007 |
| WO | 2007/146636 A1 | 12/2007 |

OTHER PUBLICATIONS

Kalpesh B. Sidhpuria, et al., "Supported ionic liquid silica nanoparticles (SILnPs) as an efficient and recyclable heterogeneous catalyst for the dehydration of fructose to 5-hydroxymethylfurfural," Green Chemistry, 13, 340-349 (2011).
Catherine A. Morris, et al. "Flexible Synthesis of Composite Aerogels," Silica Sol as a Nanoglue, vol. 284 (1999).

* cited by examiner

*Primary Examiner* — Golam M M Shameem
(74) *Attorney, Agent, or Firm* — Hoffmann & Baron, LLP

(57) ABSTRACT

In a process for carrying out a reaction, a liquid reaction mixture is contacted with a catalyst that includes silica and/or a silicate, in which process a silicon compound that is soluble in the liquid reaction mixture is added to the reaction mixture before being contacted with the catalyst. The aqueous reaction mixture suitably contains water, an alcohol or a mixture thereof.

15 Claims, No Drawings

PROCESS FOR CARRYING OUT A REACTION INVOLVING A LIQUID REACTION MIXTURE

CROSS-REFERENCE TO RELATED APPLICATIONS

This application is the National Stage of International Application No. PCT/NL2012/050932 filed Dec. 27, 2012, which claims the benefit of U.S. Provisional Application No. 61/580,845, filed Dec. 28, 2011, and Netherlands Application No. NL 2008047, filed Dec. 28, 2011, the contents of all of which are incorporated by reference herein.

FIELD OF THE INVENTION

The present invention relates to a process for carrying out a reaction involving a liquid reaction mixture wherein a catalyst that comprises silica and/or a silicate, is contacted with the liquid reaction mixture.

BACKGROUND OF THE INVENTION

In the chemical and petrochemical industry there is a wide variety of reactions wherein a liquid reaction mixture is contacted with a catalyst that comprises silica and/or a silicate. The liquid reaction mixture may comprise a liquid solvent including water, but also one or more liquid reactants. Many chemical reactions are conducted in the presence of a catalyst. Especially when the catalyst is solid, catalysts that comprises silica and/or silicates are widely used. Examples include the production of heterocyclic nitrogen compounds including piperazine and carbon-substituted alkyl derivatives, cycloaliphatic amines from cycloalkanols and morpholine and carbon-substituted alkyl derivatives (cf. U.S. Pat. No. 3,152,998) and the conversion of furan to 1,4-butanediol and tetrahydrofuran in a dicarboxylic acid and water in the presence of a catalyst of nickel/copper/chromium on a support (cf. U.S. Pat. No. 4,146,741).

Zeolites, especially aluminosilicate zeolites, are also well-known for their catalytic activity. In many chemical reactions they are being used for such reasons. In the petrochemical industry they find use as catalysts in a variety of treating reactions, including hydrocracking, hydrotreating, reforming, dewaxing and catalytic cracking of crude oil and refinery streams. Zeolites may also be used in a variety of chemical reactions, including hydration and dehydration of various chemicals, additions to and eliminations from alcohols and acids such as etherifications and esterifications, hydroformylations, oxidations, aldol condensations and additions to epoxides.

Silica may be used in a catalyst as a carrier of the catalytically active material, such as a metal compound. It may also be used as the catalytic material itself, e.g. in the form of silica-alumina, or as a binder for catalytically active material, such as a zeolite. In R. M. Ravenelle et al., J. Phys. Chem. C, 2010, 114, 19582-19595, a study has been described wherein zeolite Y and ZSM-5 were treated in liquid water at 150 to 200° C. under autogenic pressure. It was noted that zeolite Y was transformed into amorphous material. The authors do not understand the mechanism although it is suggested that the hydrolysis of siloxane bonds plays a role. They conclude that the stability of zeolite catalysts in high temperature aqueous environments needs to be considered carefully. In H. van Bekkum et al., Introduction to Zeolite Science and Practice, Elsevier, page 828, it is observed that some high silica zeolites are stable in aqueous acid medium at moderate temperatures, but that generally low silica zeolites (A, X, Y) are not stable under conditions of low pH, and care should be taken when such zeolites are used in a low pH slurry technique as catalysts. It is therefore an objective of the present inventors to find a solution to the issue around the stability of silica or silicate-containing catalysts with the concurrent loss of catalytic activity. Since, although some catalysts that contain silica and/or silicates tend to have relatively stable structures, it has been observed that in use a loss of catalyst may occur. Generally, this catalyst loss is due to attrition, such as in the case of catalytic cracking wherein a fluid stream of reactant and catalyst particles comprising zeolites and binder material, is passed through reactors causing contact between the particles which leads to attrition, to the formation of catalyst fines and ultimately to catalyst losses. Presently, it has been found that the reduction in catalytic activity when silica- or silicate-containing catalysts are used in an aqueous reaction mixture, is caused by solubilisation issues. It appeared that under certain circumstances silicate material from the catalyst is dissolved, which leads to a loss of catalyst material, and hence to a reduction in catalytic activity.

In WO 99/42214 catalyst supports that are soluble in acid or neutral aqueous solutions are treated with a modifying compound. Such a compound may comprise silicon. In such cases the support is treated with a silicon precursor by which the silicon precursor is introduced into or onto the support via impregnation, subsequent drying and calcination, so that silicon remains. The support may be alumina, titania or magnesia. Hence, this method is unsuitable for silica and/or silicates-containing catalysts.

Whereas the catalyst losses for silica and/or silicates-containing catalysts so far have been dealt with by the addition of extra fresh catalyst, it has now been found that the catalyst loss, and hence a reduction in catalytic activity can be counteracted when a silicon compound is added to the reaction mixture in question. Accordingly, the present invention provides a process for carrying out a reaction wherein a liquid reaction mixture is contacted with a catalyst that comprises silica and/or a silicate, wherein a silicon compound that is soluble in the liquid reaction mixture is added to said reaction mixture before being contacted with the catalyst.

It appeared that when a soluble silicon compound was added to the liquid reaction mixture, the dissolution problems did not occur and catalyst losses were prevented. Without wishing to be bound by any theory, it is believed that the addition of the silicon compound results in a liquid mixture wherein the solubility of the silica and/or silicate-material is limited such that any further dissolution of solid material from the catalyst is suppressed or completely prevented. It is believed that when the liquid mixture constitutes a saturated solution of the silicate material the absolute dissolution may be completely avoided.

SUMMARY OF THE INVENTION

It has been found that the dissolving of silica and/or silicate-material from the catalyst occurs especially when the liquid reaction mixture contains water and/or alcohols, in particular alcohols with 1 to 4 carbon atoms, such as methanol, ethanol, n-propanol, isopropanol, n-butanol, t-butanol, isobutanol, butanol-2 and mixtures thereof. The process according to the present invention is especially advantageous when the liquid reaction medium contains considerable amounts of water. The liquid reaction mixture may preferably contain up to 100% wt of water, suitably at least 1% wt, and up to 99% wt of water, more preferably from 5 to 95% wt, based on the total reaction mixture. The solubility of silica and silicate salts is limited in any solvent, but in aqueous environments silica may dissolve to concentration levels of over 100 ppmw. Evidently, when the liquid reaction mixture comprises water, the resulting aqueous mixture may comprise other components in addition to water. It may comprise aqueous mixtures of salts, acids, bases, but also mixtures with organic co-solvents or other organic components. Such other organic components may comprise alcohols, aldehydes, ketones, organic acids and sulphoxides, in particular alcohols in addition to water. Also when the reaction mixture comprises an alcohol, the solubility of silica or silicate-material is not negligible. The solubility effects are most noticeable when the alcohol has a relatively short carbon chain. Therefore, the alcohol has suitably from 1 to 12 carbon atoms, and more suitably 1 to 6 carbon atoms. The invention works particularly well when the alcohol is a $C_1$-$C_6$ aliphatic alcohol. The reaction mixture may therefore for example contain methanol, ethanol, propanol or methoxylate, ethoxylate or propoxylate.

DETAILED DESCRIPTION OF THE INVENTION

The solubility of the silica and silicate-material may depend on a variety of factors, including the temperature and pH of the reaction mixture. To a large extent these conditions are determined by the reaction in which the aqueous reaction mixture is being employed. Therefore, the temperature may vary within wide ranges, such as 25 to 800° C. The skilled person will realise that when the temperature exceeds 100° C., and since the aqueous reaction mixture comprises water, the pressure is also elevated to ensure that the aqueous reaction mixture remains liquid. Also when lower alcohols, i.e., $C_1$-$C_6$-alcohols, are employed in the reaction mixture, pressures may need to be elevated to ensure that the reaction mixture remains liquid.

It has been found that the dissolving of silica and silicate-material is enhanced when the pH of the aqueous reaction mixture is very low or very high. At relatively moderate pH values the solubility of the silica and silicate-material is rather limited. Therefore, the effect of the present invention is most significant when the aqueous reaction mixture has a pH of at most 2 or at least 12, more significantly, when the pH is at most 1 or at least 13.

As indicated above, it is believed that the addition of silicon compound may lead to the saturation of the silica and/or silicate-material in the aqueous reaction mixture. Therefore, it is especially advantageous if the silicon compound is added to the aqueous reaction mixture to obtain a concentration of 5 to 100 ppmw of the compound, calculated as silicon, based on the weight of the reaction mixture. More preferably, the quantity of the silicon compound is such that it results in a saturated solution thereby suppressing the dissolving of further silica and/or silicate-material optimally. Since the solubility of silica and silicate salts vary in accordance with the variation of the amounts of water and other solvents, such as alcohols, temperature and pH, the optimum amount of added silicon compound may vary accordingly.

The desired silicon compounds are preferably selected from the group consisting of silicates and silicate-forming compounds, since it is believed that the losses of the catalyst material proceeds via the formation of silicate ions that dissolve in the liquid, suitably aqueous, reaction mixture. Suitable silicon compounds include silicic acid, inorganic silicates, such as alkali metal silicates, inorganic fluorosilicates and organic orthosilicates, such as tetraalkylammoniumsilicates. Silicate-forming materials may also be used, e.g. silicon tetrahalides, which upon contact with water, may convert into silicates. Good results have been obtained with the use of tetraalkylorthosilicates as silicon compound, especially with the compounds wherein the alkyl moieties comprise from 1 to 6 carbon atoms. Suitable compounds are thus tetraethylorthosilicate and tetramethylorthosilicate. A very advantageous way of providing the desired silicon compound is by employing a bed of solid silicon dioxide (silica). In a preferred method the aqueous reaction mixture is passed via a bed of solid silicon dioxide before it is subjected to the reaction conditions, including the contact with the catalyst. In this way the aqueous reaction mixture is incorporating liquid silicates, e.g. silicic acid, from the bed of silicon dioxide up to a certain level, preferably to saturation. When the aqueous reaction mixture is subsequently exposed to the contact with the catalyst, there will be a reduced tendency, if any, for the silicate molecules in the catalyst to dissolve. Thereby the loss of catalyst is greatly, if not completely, suppressed. Hence, the silicon compound is advantageously provided by a bed of solid silicon dioxide.

The reaction may be conducted batch-wise, semi-batch-wise or in a continuous mode. In a batch mode the effect of catalyst loss is usually not very significant. The dissolution of the silicate material from the catalyst may increase to saturation levels but the loss of catalyst material tends to be rather low in absolute terms. However, the situation may be different in continuous reactions. In such reactions the aqueous reaction mixture is usually passed over a bed of solid catalyst. Therefore, there will continuously be a tendency for silicate molecules to dissolve into the freshly supplied aqueous reaction mixture. This may result in noticeable losses of silicate material that is passed along with the flow of aqueous reaction mixture. Since the effect of the invention is most pronounced in a continuous process, the reaction is suitably conducted in a continuous mode. In such respect it is not material whether the process is conducted in a trickle flow or plug flow, or whether it is conduced in an upward, downward or horizontal flow. Any continuous reaction will optimally benefit from the present invention.

The addition of the silicon compound may be done in a continuous or intermittent manner. From the above it is evident that the effect of the invention is most noticeable when the aqueous reaction mixture continuously contains a level of dissolved silica or silicate material. In a batch reaction, such continued level may be obtained by intermittent addition of silicon compound. However, when the reaction is carried out in a continuous manner, the addition of silicon compound is also preferably conducted in a continuous mode.

The catalyst that comprises silica and/or silicate may be selected from a variety of compounds. As indicated above, the silica may originate from a silica binder. Such binder is used to enable the production of stable particles that comprise the catalytically active components in a matrix of binder material. Silica may also be a catalytically active material itself, e.g. in the form of amorphous silica-alumina. However, also crystalline silica, e.g. silicalite and other zeolites that consist of pure silica may be used. Other silicate-containing material may also be useful. Many crystalline silicates are being used as catalyst, e.g., aluminosilicates, titanium silicates, cerium silicates, iron silicates, zirconium silicates, gallium silicates and other metal silicates.

Clays, such as bentonite or montmorillonite, may also be used. The skilled person will realise that the process according to the present invention can be usefully applied to any reaction where a silica- or silicate-containing catalyst in whatever form or shape may lose material owing to dissolution of silica or silicate material in an aqueous reaction mixture. It has been found that excellent results are obtainable with processes wherein a catalyst is used comprising a zeolite selected from mordenite, faujasite, ZSM-5, zeolite beta, zeolite L and zeolite A.

As indicated above the method of the present invention can be applied to any process wherein a liquid reaction mixture is contacted with a silica or silicate-containing catalyst in order to prevent loss of catalyst material. The reaction mixture may be any in which silica or a silicate may dissolve. Such reaction mixtures include the reactants of the reactions for the production of heterocyclic nitrogen compounds as described in U.S. Pat. No. 3,152,998 and the conversion of furan to 1,4-butanediol and tetrahydrofuran in a dicarboxylic acid and water in the presence of a catalyst of nickel/copper/chromium on a support, as described in U.S. Pat. No. 4,146,741. A very suitable reaction mixture comprises a saccharide, water and an alcohol. Such reaction mixture may be used for the production of alkyl ethers of furfural. This reaction has been described in WO 2007/104514. Another suitable reaction mixture comprises a saccharide, water and a carboxylic acid to form esters of furfural. This reaction has been described in WO 2007/104515. Both reactions take place in the presence of an acid catalyst, which may be a solid silica or silicate-containing catalyst.

In the above patent applications the conversion of a carbohydrate to the ether or ester, respectively, has been described wherein the saccharide is converted into the desired product in one step. Since it is advantageous to have the ether or ester of furfural been made available via the most convenient method, these compounds are preferably derived from the dehydration of a saccharide. As disclosed in the above-mentioned patent applications, the saccharide is suitably selected from polysaccharides, oligosaccharides, disaccharides and monosaccharides. The components of particular interest in biomass are those feedstocks that contain a monosaccharide. Examples of suitable monosaccharides include fructose and mixtures of fructose with other monosaccharides, such as other hexoses and/or pentoses. A hexose is a monosaccharide with six carbon atoms having the chemical formula $C_6H_{12}O_6$. Hexoses may be classified by functional group, with aldohexoses having an aldehyde at position 1, and ketohexoses having a ketone at position 2. Fructose is a ketohexose. Suitable other hexoses include but are not limited to glucose, galactose, mannose, and their oxidized derivatives, e.g. aldonic acid, reduced derivatives, e.g. alditol, etherified, esterified and amidated derivatives. A pentose is a monosaccharide with five carbon atoms, having the chemical formula $C_5H_{10}O_5$. They may either have an aldehyde functional group in position 1 (aldopentoses), or a ketone functional group in position 2 (ketopentoses). Suitable 5-carbon monosaccharides include but are not limited to arabinose, ribose, ribulose, xylose, xylulose and lyxose.

The di- and oligosaccharide carbohydrates containing more than one saccharide unit, are suitably hydrolysed, resulting in a mixture of dissolved di- and/or oligosaccharides, monomeric saccharide units and/or glycoside units. Examples of suitable disaccharides include maltose, lactose, trehalose, turanose and sucrose, sucrose being preferred. Sucrose is abundantly available and therefore very suitable. The disaccharides can easily be converted into the monomeric units. Examples of suitable oligosaccharide are fructo-oligosaccharides which are found in many vegetables. By oligosaccharides is understood a carbohydrate that is built up of 3 to 10 monosaccharide units. Polysaccharides have more than ten monosaccharide units. These are polymeric structures formed of repeating units joined together by glycosidic bonds. The number of monosaccharide units in a polysaccharide may vary widely, and may range from 10 to 3000. Suitable polysaccharides include fructan, i.e. a polymer of fructose moieties, and levan, which is composed of D-fructofuranosyl moieties. Mixtures may also be used. Starch, hemi-cellulose and in particular cellulose can also be used as starting material, especially if they stem from hydrolysis process streams from enzymatic or catalytic hydrolysis of starch, cellulose and hemi-cellulose or from alcoholysis processes that already contain mono- and disaccharides. In view of the above, the preferred monosaccharide is fructose, glucose and mixtures thereof. The preferred disaccharide is sucrose.

The invention will be further illustrated by means of the following examples.

Example I

A number of experiments was conducted to show the effectiveness of the present invention to prevent the loss of catalyst material.

Two aqueous mixtures that were contacted with solid silica or silicate-containing catalyst were prepared; Mixture 1 consisted of methanol and water (90:10 v/v), and Mixture 2 consisted of methanol and water (90:10 v/v) to which 9 g/L levulinic and 3.6 g/L formic acid was added. The mixtures were contacted with three types of catalysts: Catalyst A consisted of pure amorphous silica, Catalyst B consisted of mordenite, an aluminosilicate, in a silica matrix (80% wt aluminosilicate on dry weight basis) and Catalyst C consisted of mordenite in a titania matrix (80% wt aluminosilicate on dry weight basis). The experiments were conducted by passing the Mixtures over beds of the Catalysts at different temperatures. The beds consisted of 100 microliters, the flow rate was 62.5 microliter per min. After 168 hours the mass of the catalyst bed was determined. Temperatures differed but the pressure was 65 barg.

In two series of experiments 208 mg/L tetraethylorthosilicate (TEOS) was added, which corresponded to 60 ppmw $SiO_2$ or 28 ppmw silicon. The results are shown in Table 1.

TABLE 1

| Experiment No. | Mixture | TEOS | Temp. (° C.) | Catalyst | Catalyst loss (% wt) |
|---|---|---|---|---|---|
| 1 | 1 | − | 40 | A | 0 |
| 2 | 1 | − | 40 | B | 0 |
| 3 | 1 | − | 40 | C | 0 |
| 4 | 1 | − | 180 | A | 93 |
| 5 | 1 | − | 180 | B | 39 |
| 6 | 1 | − | 180 | C | 0 |
| 7 | 1 | + | 180 | A | 65 |
| 8 | 1 | + | 180 | B | 4 |
| 9 | 1 | + | 180 | C | 3 |
| 10 | 2 | − | 180 | A | 56 |
| 11 | 2 | − | 180 | B | 50 |
| 12 | 2 | − | 180 | C | 35 |
| 13 | 2 | + | 180 | A | 0 |
| 14 | 2 | + | 180 | B | 0 |
| 15 | 2 | + | 180 | C | 0 |

The results show that the loss of silica is influenced by temperature and presence of acid. The results further show that addition of TEOS suppresses the loss of silica and silicates.

Example II

A second series of experiments was conducted with an aqueous reaction mixture that contained 20% wt fructose in a methanol/water mixture (95:5 v/v). Under the reaction conditions fructose was converted to methoxymethylfurfural (MMF). The reaction mixture was passed over Catalyst B or C at a temperature of 180° C. and a pressure of 65 barg. After 72 hours on stream, the reaction was stopped and the reactor freed from volatiles. Subsequently, the catalyst was calcined by exposing the catalyst to an air flow at 500° C. for 4 hours to remove any carbonaceous deposit thereon. This routine was repeated a number of times. After the last cycle the loss of catalyst material was determined (expressed as percentage of the original catalyst) as well as the relative yield of MMF at the beginning of the cycle in question (expressed as percentage of the yield at the start of the first cycle).

In a series of experiments 208 mg/L TEOS was added to the reaction mixture that was passed over the bed of catalyst.

The number of cycles used and the results for Catalysts B and C are shown in Table 2.

TABLE 2

| Exp. No. | Catalyst | Number of cycles | without TEOS addition | | with TEOS addition | |
|---|---|---|---|---|---|---|
| | | | Catalyst loss, % wt | MMF yield, % | Catalyst loss, % wt | MMF yield, % |
| 16 | B | 3 | 48 | 69 | 0 | 91 |
| 17 | B | 4 | 60 | 66 | 0 | 97 |
| 18 | B | 5 | 67 | 34 | 0 | 94 |
| 19 | C | 4 | 39 | 88 | 0 | 94 |

Example III

A third series of experiments was conducted with a liquid reaction mixture that contained 20% wt fructose in a methanol/water mixture (95:5 v/v). Under the reaction conditions fructose was converted to methoxymethylfurfural (MMF). The reaction mixture was passed over Catalyst B at a temperature of 180° C. and a pressure of 65 barg. After 72 hours on stream, the catalysts were calcined by exposing the catalyst to an air flow at 500° C. for 4 hours. The loss of catalyst material was determined.

For experiment 20 the reaction mixture was used neat, then for experiments 21 to 24 different sources of soluble silica were added to the reaction mixture and passed over the bed of catalyst. For experiment 21, 170 mg/L of silicon tetrachloride ($SiCl_4$) was added. For experiment 22, 152 mg/L of tetramethylorthosilicate (TMOS) was added. For experiment 23, 208 mg/L of tetraethylorthosilicate (TEOS) was added. For experiment 24, 1142 mg/mL of tetramethylammonium silicate was added.

The results for Catalyst B losses are shown in Table 3.

TABLE 3

| Exp. No. | Si source | Catalyst B loss, % wt |
|---|---|---|
| 20 | None | 20 |
| 21 | silicon tetrachloride ($SiCl_4$) | 2 |
| 22 | tetramethylorthosilicate (TMOS) | 4 |
| 23 | tetraethylorthosilicate (TEOS) | 0 |
| 24 | tetramethylammonium silicate | 0 |

Example IV

In order to show that the optimal value of the silicon source has to be determined depending on reaction conditions, a fourth series of experiments was conducted with a liquid reaction mixture that contained 20% wt fructose in a methanol/water mixture (95:5 v/v). Under the reaction conditions fructose was converted to methoxymethylfurfural (MMF). The reaction mixture was passed over Catalyst B. TEOS concentration, LHSV and temperature of 180° C. were changed. Pressure was 75 barg for all experiments. After 72 hours on stream, the catalysts were calcined by exposing the catalyst to an air flow at 500° C. for 4 hours. The loss of catalyst material was determined.

The results and conditions are given in Table 4.

Example V

Another experiment, No. 58, was conducted with an aqueous reaction mixture that contained 20% wt fructose in a methanol/water mixture (95:5 v/v) containing 208 mg/L TEOS. Under the reaction conditions fructose was converted to methoxymethylfurfural (MMF), hydroxymethylfurfural (HMF), methyl levulinate (ML) and furfural (F). The reaction mixture was passed over Catalyst B (Mordenite 90 from Zeolyst CBV-90 with a 20% wt $SiO_2$ binder) at a LHSV of 37.5 1/h, a temperature of 220° C. and a pressure of 75 barg. The yields obtained are presented in Table 5.

TABLE 5

| Time on stream (h) | MMF Yield (%) | MMF + HMF + ML + F Yield (%) |
|---|---|---|
| 1 | 39.5 | 75.3 |
| 2.5 | 46.6 | 83.9 |
| 26 | 45.9 | 78.7 |

TABLE 4

| Exp. No. | TEOS Conc. (mg/L) | LHSV (1/h) | Temperature (° C.) | Weight loss (%) |
|---|---|---|---|---|
| 25 | 0 | 75 | 180 | 22 |
| 26 | 0 | 37.5 | 180 | 15 |
| 27 | 0 | 25 | 180 | 13 |
| 28 | 0 | 75 | 200 | 30 |
| 29 | 0 | 37.5 | 200 | 20 |
| 30 | 0 | 25 | 200 | 16 |
| 31 | 0 | 75 | 220 | 25 |
| 32 | 0 | 37.5 | 220 | 21 |
| 33 | 0 | 25 | 220 | 15 |
| 34 | 52 | 75 | 200 | 20 |
| 35 | 52 | 37.5 | 200 | 13 |
| 36 | 52 | 25 | 200 | 10 |
| 37 | 52 | 75 | 220 | 19 |
| 38 | 52 | 37.5 | 220 | 12 |
| 39 | 52 | 25 | 220 | 11 |
| 40 | 104 | 75 | 180 | 7 |
| 41 | 104 | 37.5 | 180 | 5 |
| 42 | 104 | 25 | 180 | 5 |
| 43 | 104 | 75 | 200 | 13 |
| 44 | 104 | 37.5 | 200 | 9 |
| 45 | 104 | 25 | 200 | 7 |
| 46 | 104 | 75 | 220 | 16 |
| 47 | 104 | 37.5 | 220 | 10 |
| 48 | 104 | 25 | 220 | 8 |
| 49 | 208 | 75 | 180 | 3 |
| 50 | 208 | 37.5 | 180 | 2 |
| 51 | 208 | 25 | 180 | 2 |
| 52 | 208 | 75 | 200 | 6 |
| 53 | 208 | 37.5 | 200 | 4 |

TABLE 4-continued

| Exp. No. | TEOS Conc. (mg/L) | LHSV (1/h) | Temperature (° C.) | Weight loss (%) |
|---|---|---|---|---|
| 54 | 208 | 25 | 200 | 4 |
| 55 | 208 | 75 | 220 | 10 |
| 56 | 208 | 37.5 | 220 | 5 |
| 57 | 208 | 25 | 220 | 5 |

The invention claimed is:

1. A process for carrying out a reaction wherein a crystalline silicate is being used as catalyst and wherein a liquid reaction mixture, which comprises water, is contacted with the catalyst, wherein a silicon compound that is soluble in the liquid reaction mixture is added to said reaction mixture before being contacted with the catalyst, wherein the silicon compound is selected from the group consisting of silicic acid, inorganic silicates, inorganic fluorosilicates and organic orthosilicates.

2. The Process according to claim 1, wherein the liquid reaction mixture contains up to 99% wt of water.

3. The Process according to claim 1, wherein the liquid reaction mixture comprises an alcohol in addition to water.

4. The Process according to claim 3, wherein the alcohol is selected from $C_1$-$C_6$ aliphatic alcohols.

5. The Process according to claim 1, wherein the silicon compound is added to get a concentration of 5 to 100 ppmw of the compound, calculated as silicon, based on the weight of the reaction mixture.

6. The Process according to claim 1, wherein the organic orthosilicates are selected from tetraalkylorthosilicates.

7. The Process according to claim 1, wherein the silicon compound is provided by a bed of solid silicon dioxide.

8. The Process according to claim 1, wherein the reaction is conducted in a continuous mode.

9. The Process according to claim 1, wherein the silicon compound is added continuously or intermittently.

10. The Process according to claim 1, wherein the catalyst comprises a zeolite selected from the group consisting of mordenite, faujasite, ZSM-5, zeolite beta, zeolite L and zeolite A.

11. The Process according to claim 1, wherein the reaction mixture comprises a saccharide, water and an alcohol or a carboxylic acid.

12. The Process according to claim 11, wherein the saccharide is selected from mono-, di-, oligo- and polysaccharides.

13. The Process according to claim 12, wherein the saccharide is selected from the group consisting of fructose, glucose and sucrose.

14. The process according to claim 1, wherein the catalyst is a crystalline aluminosilicate.

15. The Process according to claim 6, wherein the tetraalkyl orthosilicates have alkyl moieties that comprise from 1 to 6 carbon atoms.

* * * * *